US012364875B2

(12) United States Patent
Galle (10) Patent No.: US 12,364,875 B2
(45) Date of Patent: Jul. 22, 2025

(54) VIEWING APPARATUS AND METHOD FOR PROJECTING A LIGHT SIGNAL

(71) Applicant: GENSIGHT BIOLOGICS, Paris (FR)

(72) Inventor: Charlie Galle, Paris (FR)

(73) Assignee: GENSIGHT BIOLOGICS, Paris (FR)

( * ) Notice: Subject to any disclaimer, the term of this patent is extended or adjusted under 35 U.S.C. 154(b) by 786 days.

(21) Appl. No.: 17/607,113

(22) PCT Filed: Apr. 29, 2020

(86) PCT No.: PCT/EP2020/061898
§ 371 (c)(1),
(2) Date: Oct. 28, 2021

(87) PCT Pub. No.: WO2020/221803
PCT Pub. Date: Nov. 5, 2020

(65) Prior Publication Data
US 2022/0203119 A1    Jun. 30, 2022

(30) Foreign Application Priority Data

May 2, 2019   (EP) .................................... 19305561

(51) Int. Cl.
*A61N 5/06*    (2006.01)
*F21V 8/00*    (2006.01)
*G02B 27/01*   (2006.01)

(52) U.S. Cl.
CPC ......... *A61N 5/0622* (2013.01); *G02B 6/0003* (2013.01); *G02B 6/0005* (2013.01);
(Continued)

(58) Field of Classification Search
CPC .................. A61H 3/061; A61N 5/0622; A61N 2005/0632; A61N 2005/0648;
(Continued)

(56) References Cited

U.S. PATENT DOCUMENTS 6,149,272 A    11/2000  Bergner et al.
6,829,095 B2   12/2004  Amitai
(Continued)

FOREIGN PATENT DOCUMENTS

JP       H10272098 A      10/1998
WO    WO 2007/024391      3/2007
(Continued)

OTHER PUBLICATIONS

International Search Report for PCT/EP2020/061898 dated Jun. 4, 2020.
European Search Report for EP 19 30 5561 dated Oct. 15, 2019.

*Primary Examiner* — Nelson M Rosario
(74) *Attorney, Agent, or Firm* — B. Aaron Schulman, Esq.; Stites & Harbison, PLLC (57) ABSTRACT

The present invention concerns a viewing apparatus comprising:
  a first optical line comprising:
    a projecting system adapted to project a light signal on a first area of the retina of an eye of a wearer of the viewing apparatus,
    a light signal generator generating the light signal to be projected, and
    a waveguide comprising an input coupler and an exit coupler, the waveguide being adapted to convey light from the input couple to the exit coupler, and optionally a second optical line comprising an optical system adapted to project a light signal of the environment on a second area of the retina of the eye of the wearer, the optical system comprising a part of the waveguide.

18 Claims, 2 Drawing Sheets

(52) U.S. Cl.
CPC ............... *A61N 2005/0632* (2013.01); *A61N 2005/0648* (2013.01); *A61N 2005/0664* (2013.01); *G02B 27/0172* (2013.01)

(58) Field of Classification Search
CPC .... A61N 2005/0662; A61N 2005/0664; G02B 27/0172; G02B 6/0003; G02B 6/0005
See application file for complete search history.

(56) References Cited

U.S. PATENT DOCUMENTS

| | | | |
|---|---|---|---|
| 8,906,360 | B2 | 12/2014 | Deisseroth et al. |
| 10,394,034 | B2 * | 8/2019 | Reshidko ............. G06V 40/197 |
| 11,320,649 | B2 | 5/2022 | Chavas et al. |
| 2003/0165017 | A1 | 9/2003 | Amitai |
| 2006/0228073 | A1 | 10/2006 | Mukawa et al. |
| 2009/0088399 | A1 | 4/2009 | Balya et al. |
| 2013/0005795 | A1 | 1/2013 | Balya et al. |
| 2014/0094506 | A1 | 4/2014 | Bayla et al. |
| 2014/0121265 | A1 | 5/2014 | Pan et al. |
| 2015/0205135 | A1 * | 7/2015 | Border ................ B32B 37/1284 359/630 |
| 2015/0246094 | A1 | 9/2015 | Lagali et al. |
| 2017/0111619 | A1 | 4/2017 | Benosman et al. |
| 2018/0157042 | A1 * | 6/2018 | Wall ................... G02B 27/0172 |
| 2018/0172981 | A1 | 6/2018 | Ishii |
| 2019/0269755 | A1 | 9/2019 | Pruneau et al. |
| 2019/0324275 | A1 * | 10/2019 | Nishizawa ............ G06F 9/3004 |
| 2020/0110265 | A1 * | 4/2020 | Serdarevic ........... A61B 3/0008 |
| 2021/0149188 | A1 | 5/2021 | Chavas et al. |

FOREIGN PATENT DOCUMENTS

| | | |
|---|---|---|
| WO | WO 2009/127705 | 10/2009 |
| WO | WO 2013/071231 | 5/2013 |
| WO | WO 2014/151877 | 9/2014 |

* cited by examiner

VIEWING APPARATUS AND METHOD FOR PROJECTING A LIGHT SIGNAL

TECHNICAL FIELD OF THE INVENTION

The present invention concerns a viewing apparatus and a method for projecting light signal.

BACKGROUND OF THE INVENTION

The solution aims at stimulating retinal ganglion cells in the context of an optogenetics therapy.

The retina is composed of photoreceptors, which are highly specialized neurons that are responsible for photosensitivity of the retina by phototransduction, i.e. the conversion of light into electrical and chemical signals that propagate a cascade of events within the visual system, ultimately generating a representation of world. In the vertebrate retina, phototransduction is initiated by activation of light-sensitive receptor protein, rhodopsin.

Photoreceptor loss or degeneration, such as in case of retinitis pigmentosa (RP) or macular degeneration (MD), severely compromises, if not completely inhibits, phototransduction of visual information within the retina. Loss of photoreceptor cells and/or loss of a photoreceptor cell function are the primary causes of diminished visual acuity, diminished light sensitivity, and blindness.

Several therapeutic approaches dedicated to retinal degenerative diseases are currently in development, including gene therapy, stem cell therapy, optogenetics, and retinal prostheses.

For example it has been proposed to restore photosensitivity of the retina of a subject by controlling activity of defined populations of neurons without affecting other neurons in the brain by gene- and neuroengineering technology termed optogenetics. In contrast to traditional gene therapy that attempts to replace or repair a defective gene or bypass the genetic defect through correction of the protein deficiency or dysfunction, optogenetic approaches can be used to endow normally non-photosensitive cells in the retina with the ability to respond to light, thus restoring useful vision to the patient. Unlike retinal chip implants that provide extracellular electrical stimulation to bipolar or ganglion cells, optogenetics-based therapies stimulate the cells from inside the cell.

Optogenetics refers to the combination of genetics and optics to control well-defined events within specific cells of living tissue. Optogenetics consists in (i) genetically modifying target cells in order to render them sensitive to light by the expression of exogenous photoreactive proteins in cellular membrane and (ii) providing illuminating device able to provide light to said photoreactive proteins.

Examples of exogenous photoreactive proteins are provided in WO2007024391, WO2008022772 or WO2009127705 which describe the use of opsin genes derived from plants and microbial organisms (e.g. archaebacteria, bacteria, and fungi) encoding light-activated ion channels and pumps (e.g. channelrhodopsin-2 [ChR2]; halorhodopsin [NpHR]), engineered for expression in mammalian neurons and which can be genetically targeted into specific neural populations using viral vectors. When exposed to light with appropriate wavelength, action potentials can be triggered in opsin-expressing neurons conferring thereby light sensitivity to these cells. Similarly, WO2013071231 discloses new channelrhodopsins, Chronos and Chrimson, which have different activation spectra from one another and from the state of the art (e.g., ChR2/VChR1), and allow multiple and distinct wavelengths of light to be used to depolarize different sets of cells in the same tissue, by expressing channels with different activation spectra genetically expressed in different cells, and then illuminating the tissue with different colors of light. The photoreactive protein disclosed in WO2017187272 is another alternative.

Optogenetics is an extremely powerful tool for selective neuronal activation/inhibition which can, for example, be used to restore neural functions in living animals, including humans, particularly in the eye.

Nevertheless, it has been shown that selected wavelengths of light shall be close to the optimal wavelengths of the photoreactive proteins and that these photoreactive proteins have a very low sensitivity to light. Therefore in order to obtain minimum level of protein activation by light, the intensity of light received by the target cell or protein shall be above a minimum value. As a consequence, an external device providing sufficient irradiance at the right wavelength is mandatory.

Alternatively, it has been proposed to restore at least partially vision in these patients with visual prosthesis systems. These systems are comprising a retina implant and are helpful tools for at least partially re-establishing a modest visual perception and a sense of orientation for blind and visually impaired users by exploiting said fact that although parts of the retinal tissue have degenerated most of the retina may remain intact and may still be stimulated directly by light dependent electrical stimuli. Typically, retina implant is implanted into the patient's eye, effecting electrical excitation of the remaining neuronal cells upon light stimulation. When being stimulated, these remaining neuronal cells convey the artificially induced electrical impulses to the visual part of the brain through the optic nerve.

Retinal implants can be broadly divided into two categories: epi- and sub-retinal. Epi-retinal devices are placed on or near the inner surface of the retina, i.e. the side of the retina which is first exposed to incident light and along which the nerve fibers of the ganglion cells pass on their way to the optic nerve. Epi-retinal implants typically comprise a chip with a plurality of pixel elements capable of receiving an image projected by an extraocular device (typically a camera and a microelectronic circuit for decoding incident light) on the retina through the lens of the eye, for converting the image into electrical signals and for further conveying the signals into electrical stimuli via a plurality of stimulation electrodes to stimulate the retinal cells adjacent the chip, in order to reconstruct or improve vision of blind or partially blind patients. In contrast, sub-retinal devices are placed under the retina, between the retina and the underlying retinal pigment epithelium or other deeper tissues. Currently available sub-retinal technologies rely on the implantation of a single, rigid and typically planar chip. It has been further shown that it is desirable to be able to implant more than one chip in order to cover a large visual field.

Retinal prostheses and optogenetic therapies rely on two main components. The first component engineered on the retina provides light sensitivity by providing a change of membrane potential of target retina cells: it is the implant in retinal prosthesis system or the light-gated ion channel protein genetically introduced in the retinal cells in optogenetic therapies. A second component is required to encode visual information (usually acquired with a camera or array of photodiodes) and to translate it in an input signal required by the former component. In retinal prostheses, the input signal is an electrical current delivered by a matrix of active electrodes or a pulse of light capable of activating passive components. In optogenetic gene therapy, the input signal which is delivered is a pulse of light at the appropriate intensity and wavelength required to activate the optogenetic protein in a defined spatio-temporal manner.

The irradiance needed of the light cannot be achieved with standard headsets.

In particular, known solutions comprises projector to project images on the retina but it doesn't allow a field of view of more than 10° which is insufficient in some cases.

Moreover, heat produced by the required powerful light source and the control electronics induces a temperature increase that has to be kept within the bounds set by the standard ISO 60601-1 for Medical Electrical Equipment. The device shall also guarantee electrical safety (ISO 60601-1) and electro-magnetic compatibility (ISO 60601-1-2, ISO 60601-1-9).

Furthermore, an increase of temperature and of heat transfer of the device in front of the eye may induce dry eye and discomfort. Thus, further temperature constraints are required on the part of the device next to the eye.

It is desirable to provide a viewing apparatus able to deliver a larger field of view with a sufficient light intensity, while maintaining a sufficient level of comfort, particularly in terms of temperature for the wearer.

More specifically, it is desirable to provide a viewing apparatus able to limit excessive thermal energy from the light source and the control electronics and/or to facilitate dissipation of heat, so as to prevent a temperature of the illuminating device from going beyond the maximum temperature of normal operation thereof and providing an enlarged field of view.

It is further desirable to provide an illuminating device which is miniaturized so that it can be worn by humans on a daily basis.

SUMMARY OF THE INVENTION

There is therefore a need for a viewing apparatus adapted to project light signal on an eye of the wearer of the apparatus which enables to obtain an enlarged field of view, being more compact and providing an improved comfort and perception for the wearer.

To the end, the specification proposes a viewing apparatus comprising a first optical line comprising (i) a projecting system adapted to project a first light signal on a first area of the retina of an eye of a wearer of the viewing apparatus, (ii) a light signal generator generating the said first light signal to be projected and (iii) a waveguide comprising an input coupler and an exit coupler, the waveguide being adapted to convey light from the input coupler to the exit coupler.

According to preferred embodiment, the viewing apparatus further comprises a second optical line comprising an optical system adapted to project a second light signal of the environment (i.e. environment light signal) towards a second area of the retina of the eye of the wearer.

According to further aspects of the invention which are advantageous but not compulsory, the viewing apparatus might incorporate one or several of the following features, taken in any technically admissible combination:
- the light signal generator comprises a total internal reflection prism (TIR prism) adapted to steer an incident light beam with an angle, the angle being preferably comprised between 20° and 40°.
- the light signal generator comprises a total internal reflection prism (TIR prism) with a digital micromirror device (DMD) imager.
- the first and second optical lines are arranged so that the intersection between the first area and the second area is void.
- the first and second optical lines are arranged so that the second area surrounds the first area.
- a main direction of light conveyance is defined for the waveguide, and the second optical line and the waveguide are arranged so that the light in the second optical line propagates along a general direction which is perpendicular to the said main direction of light conveyance of the waveguide.
- the said waveguide is made from translucent material, preferably from a transparent material.
- the first optical line is a folded line.
- the second optical line is an unfolded line.
- the light signal generator comprises a light source,
- the light signal generator comprises a light source and the first optical line is comprising: a collimating lens, the total internal reflection prism (TIR prism), a digital micromirror device (DMD) imager, and a projecting lens.
- the light signal generator comprises a light source and the light source is a fibered source,
- the light signal generator comprises a light source and the light source is an electroluminescent diode, more particularly a light-emitting diode (LED) or LED derivatives (e.g. OLED).
- the light source of the second light signal is environment of the wearer.
- the viewing apparatus is part of or consists in or is associated with googles,
- the viewing apparatus is an apparatus for optogenetics uses.
- the viewing apparatus is a virtual reality apparatus.
- the second optical line is parallel to the gaze direction of the eye of the wearer.
- the field of view of the projecting system extends between 15° and 25° along a first direction and between 25° and 35° along a second direction perpendicular to the first direction.

The specification also relates to a method for projecting light signal in an eye of the wearer of a viewing apparatus comprising a first optical line comprising (i) a projecting system adapted to project a first light signal on a first area of the retina of an eye of the said apparatus wearer, (ii) a light signal generator generating the said first light signal to be projected, and (iii) a waveguide comprising an input coupler and an exit coupler, the waveguide being adapted to convey light from the input coupler to the exit coupler. According to preferred embodiment, the viewing apparatus used in the method of the Invention further comprises a second optical line comprising an optical system adapted to project a second light signal of the environment on a second area of the retina of the eye of the wearer.

According to particularly preferred embodiment, the method comprises simultaneously the step of projecting a first light signal with the first optical line and of projecting an environment light signal with the second optical line.

BRIEF DESCRIPTION OF THE DRAWINGS

The invention will be better understood on the basis of the following description which is given in correspondence with the annexed figures and as an illustrative example, without restricting the object of the invention. In the annexed figures.

DETAILED DESCRIPTION OF SOME EMBODIMENTS

Figure 1:
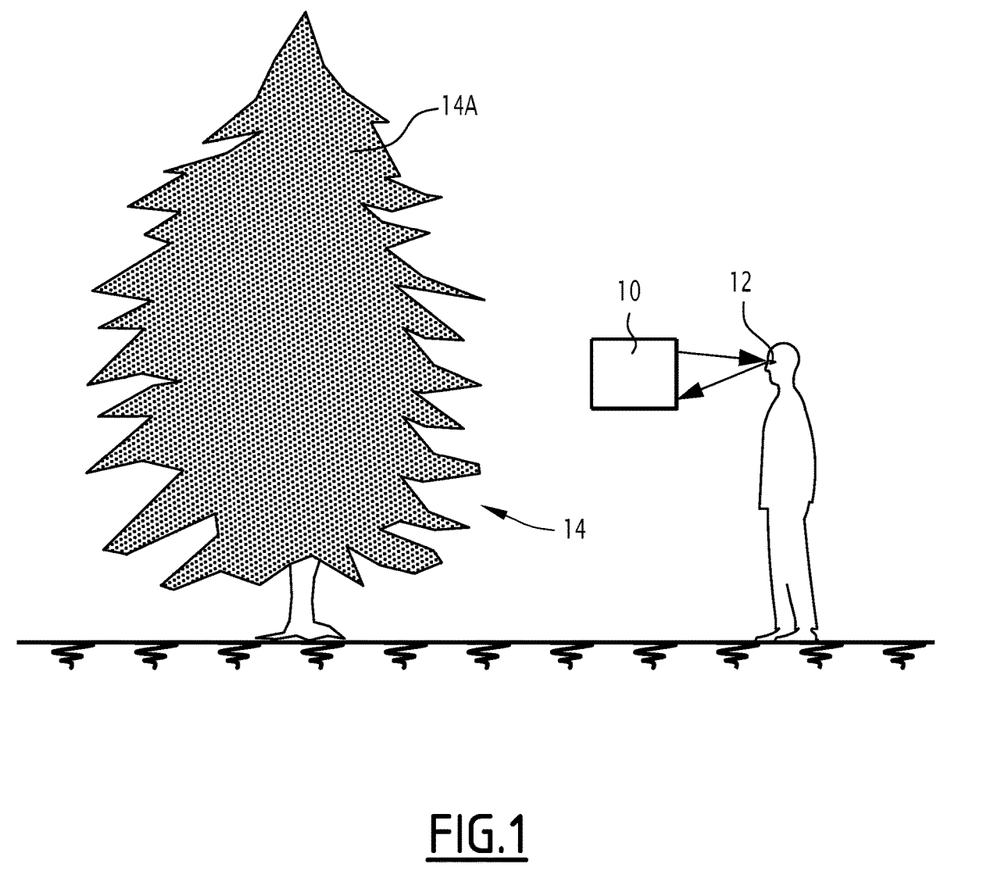
FIG. 1 shows schematically an example of viewing apparatus in a context of use by a wearer.

A viewing apparatus 10, a wearer 12 and a part of the environment 14 of the wearer 12 are represented on FIG. 1. The part of the environment comprises trees 14A.

A viewing apparatus 10 is an apparatus used by the wearer 12 of said apparatus 10 for viewing the part 14 of the environment.

Figure 2:
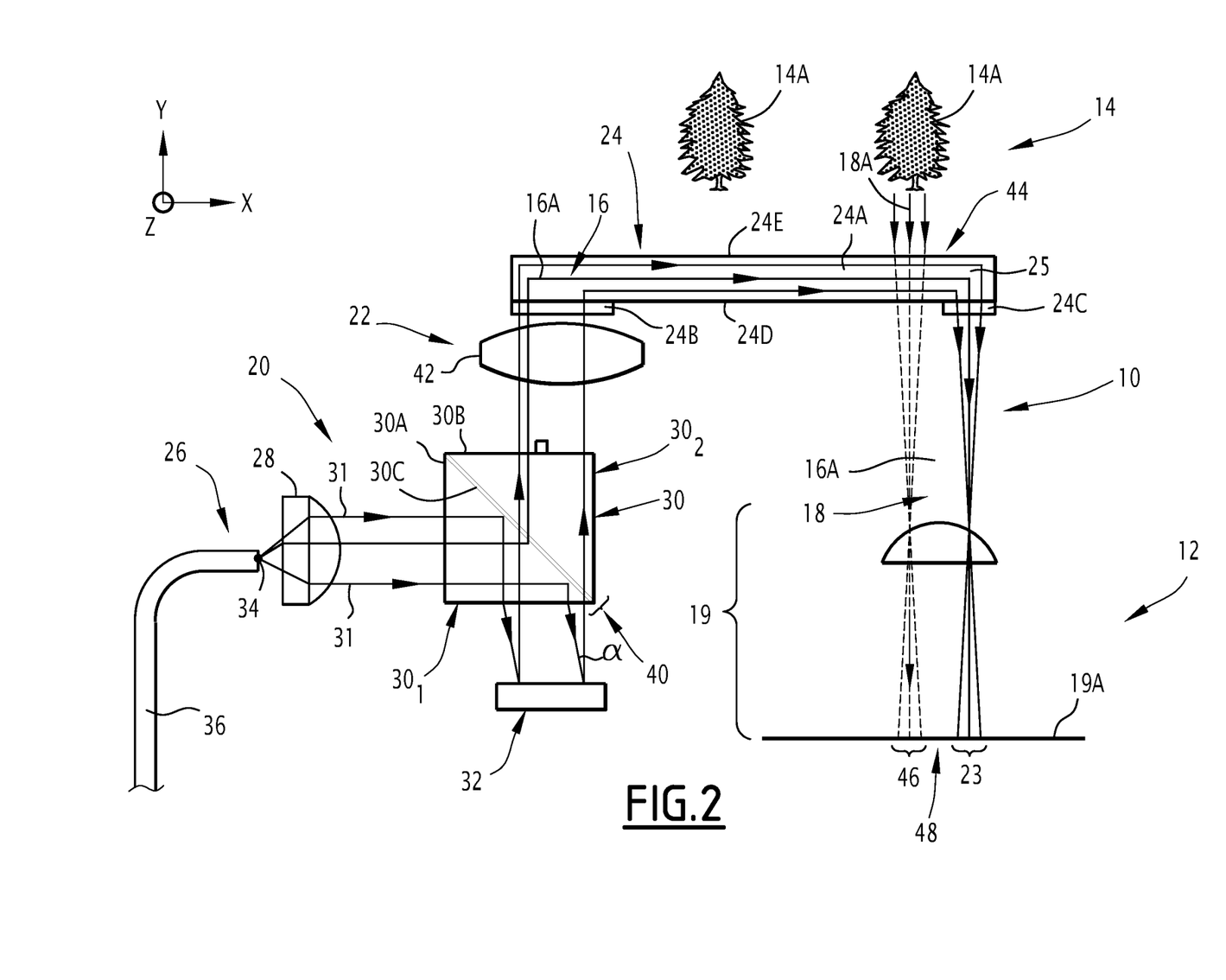
FIG. 2 is a detailed view in section of the viewing apparatus of FIG. 1.

An example of specific viewing apparatus 10 is further detailed on FIG. 2.

A first direction parallel to axis X and called "first direction X" is defined. A second direction parallel to axis Y and perpendicular to axis X is defined and called "second direction Y". A third direction parallel to axis Z and perpendicular to axis X and Y is defined, and called "third direction Z".

The viewing apparatus 10 comprises two optical lines, a first optical line 16 and a second optical line 18.

An optical line is the set of elements along the optical line that link a source of light signal to the eye 19 of the wearer 12.

According to preferred embodiments of the invention, said light signal is an image.

The first optical line 16 is a folded line.

It is understood by "folding line" that elements are arranged in such a manner that a light beam along the first optical path has a polygonal chain 16A.

The first optical line 16 comprises a light signal generator 20, a projecting system 22, and a waveguide 24.

The light signal generator 20 is adapted to generate the first light signal to be projected.

The light signal generator 20 comprises a light source 26, a collimating lens 28, a total internal reflection (TIR) prism 30 and a digital micromirror device (DMD) whose reference sign is 32.

In some cases, the wording DMD imager can be found for element 32.

According to the example of FIG. 2, the path of the light in the first optical line 16 follows the path of elements 26, 28, 30, 32, 30.

The light source 26 comprises a light-emitting element 34 adapted to generate light.

The generated light is selected according to the use of the viewing apparatus of the Invention. For example, in the case of the use of the viewing apparatus by a person equipped with a retina implant with photodiodes, the light-emitting element will be adapted so as to generate a light intensity that stimulates the photodiodes of the implant. Likewise, in the case of the use of the viewing apparatus by a person who has benefitted from optogenetic treatments, the light-emitting element will be adapted to provide a light intensity at wavelengths specific to this application, which stimulate the treated zone.

The light-emitting element 34 is therefore chosen with in particular a spectral range and/or an intensity corresponding to the application envisaged. The light-emitting element 34 may for example be a laser source or a non-coherent light source.

According to preferred embodiment, the light-emitting element 34 is a non-coherent light source.

For example, the light-emitted element 34 comprises an electroluminescent diode, more particularly a light-emitting diode (LED) or LED derivatives (e.g. OLED).

In the specific example, the light source 26 also comprises a light fiber 36 to convey light to the light emitting element 34.

More precisely and as a particular example, the light source 26 is an electroluminescent diode (not shown) which is followed by an optical fiber 36.

In other words, the light source 26 is a fibered LED.

According to preferred embodiment, the light-emitting element 34 is adapted to provide a light at wavelength able to depolarize cell that includes a light-activated ion channel polypeptide. Exemplary wavelengths of light that may be used to depolarize a cell expressing a light-activated ion channel polypeptide, include wavelengths from at least about 365 nm, 385 nm, 405 nm, 425 nm, 445 nm, 465 nm, 485 nm, 505 nm, 525 nm, 545 nm, 565 nm, 585 nm; 590 nm, 605 nm, 625 nm, 645 nm, 665 nm, 685 nm; and 700 nm, including all wavelengths therebetween. In preferred embodiments, light-emitting element 34 is adapted to provide a light intensity at wavelengths in a range of 365 nm to 700 nm, preferably ranging from 530 nm to 640 nm, preferably ranging from 580 nm to 630 nm, preferably ranging from 530 nm to 610 nm, and more particularly the light wavelength is about 595 nm.

As used herein, the term "about" when used in conjunction with numerical amount, means plus or minus 10% of that numerical amount.

The collimating lens 28 is adapted to collimate incident light beams 31 coming from the light source 26.

The light beams 31 emerging from the collimating lens 28 are substantially parallel to each other along the first direction X.

For example, the collimating lens 28 has a focal length selected in the range of 2 millimeters (mm) and 20 mm, more specifically in the range of 3 mm and 18 mm, even more particularly the collimating lens 28 has a focal length of about 5.9 mm.

A total internal reflection prism is often named TIR prism by using the acronym of Total Internal Reflection. TIR prisms are well known in the art.

The TIR prism 30 is adapted to steer an incident light 31 beam with an angle $\alpha$, named in what follows the "steering angle $\alpha$".

The TIR prism 30 comprises an input face 30A, an output face 30B, a reflection face 30C, an incident prism $30_1$ and an output prism $30_2$.

The incident face 30A receives the incident light beam.

The light beam outputs the TIR prism 30 by the output face 30B.

The input face 30A and the output face 30B are for example perpendicular to each other.

The steering angle $\alpha$ is the angle between the light beam emerging from prism $30_1$ and the normal to the digital micromirror device 32.

The steering angle $\alpha$ is for example comprised between 20° and 40°.

By definition, $\alpha$ comprised between the values A and B means that, on the one hand, $\alpha$ is superior or equal to the value A and that a is inferior or equal to the value B.

In a specific embodiment, the steering angle $\alpha$ is equal to 24°.

The incident face 30A belongs to the input prism $30_1$ and the output face 30B belongs to the output prism $30_2$.

The reflection face 30C belongs to the input prism $30_1$.

Input prism $30_1$ and an output prism $30_2$ have complementary faces.

A tiny gap 40 is defined between the input prism $30_1$ and the output prism $30_2$. The tiny gap 40 is defined between their complementary faces.

A digital micromirror device 32 is often named DMD by using the acronym of Digital Micromirror Device.

DMD are well known in the art. DMD comprises an array (e.g. 608×684 array or 912×1140 array) of mirrors that can switch regularly (e.g. every 0.35 millisecond (ms)) between two discrete angular positions named ON and OFF, with the ON position reflecting the incoming light towards the target. Processed events are encoded by setting the corresponding mirror ON.

The digital micromirror device 32 is arranged in the optical path of the light beam reflected by the reflected face 30C of the input prism $30_1$ and adapted to reflect at least a part of the light beam toward the output prism $30_2$.

A digital micromirror device 32 enables or disables a certain number of pixels in order to form the light signal to be projected.

The digital micromirror device 32 comprises a plurality of mirrors that forms arrays of micromirrors.

Each mirror has at least two positions.

In a first position, the mirror reflects light beams toward the output prism $30_2$ such that the light is transmitted to the output prism $30_2$ and emerges from the output face 30B.

In a second position, the mirror reflects light beams in such a way that no light is outputted from the output face 30B.

The projecting system 22 is adapted to project a first light signal on a first area 23 of the retina 19A of an eye 19 of the wearer 12 of the viewing apparatus 10.

In the example, the projecting system 22 is a projecting lens 42.

The field of view of the projecting system extends between 15° and 25° along a first direction and between 25° and 35° along a second direction perpendicular to the first direction.

The waveguide 24 comprises a body 24A, an input coupler 24B and an exit coupler 24C.

The waveguide 24 is adapted to convey light from the input coupler 24B to the exit coupler 24C.

According to preferred embodiment, all or part of the body 24A of the waveguide 24 is made from a translucent material.

In the following description, the term "translucent" refers to a light-transmitting body with a light transmission rate between 5% and 100%.

More preferably, all or part of the body 24A is made from a transparent material.

The term "transparent" refers to light-transmitting body with a light transmission rate greater than 95%, for example close to 100%. In particular, such a "transparent" body transmits light by refraction and through which objects are clearly visible.

Light in the waveguide 24 is composed of electromagnetic waves whose wavelength is between 500 nanometers (nm) and 700 nm.

Moreover, the body 24A of the waveguide is a parallelepiped.

In the example of FIG. 2, a main direction is defined for the waveguide 24 defined by the length of the body 24A of the waveguide 24. Such main direction is a main direction for light conveyance by the waveguide 24.

An inside face 24D and an exterior face 24E is defined for the body. The inside face 24D and the exterior face 24E are normal to the second direction Y.

The inside face 24D is intended to be directed toward the projector system 22 of the viewing apparatus and the eye 19 of the wearer when the viewing apparatus is worn.

The exterior face 24E is intended to be directed toward the part of the environment 14.

In the particular example of FIG. 2, the main direction is along the first direction X.

The input coupler 24B and the output coupler 24C are arranged on the inside face 24D of the body 24A.

For example, the input coupler 24B is arranged at an extremity of the inside face 24D and the output coupler 24C is arranged at the other extremity of the inside face 24D along the main direction.

The input coupler 24B is facing the projecting lens 42.

The input coupler 24B forms an incidence zone of the waveguide 24 whereby the light beams exiting the projector system 22 enters.

This input coupler 24B comprises a surface treatment of a part of the inside face 24D of the body 24A.

The input coupler 24B is made from a thin film in polymer.

By definition, a thin film is a film whose thickness is inferior to 10 micrometers (μm). By definition, an object is made in polymer when the content of the material of the object in polymer is superior or equal to 80%.

According to special embodiment, said polymer is silver halide.

The exit coupler 24C is facing the eye 19 of the wearer 12.

The exit coupler 24C forms an output zone of the waveguide 24.

This output coupler 24C comprises a surface treatment of a part of the inside face 24D of the body 24A.

The exit coupler 24C is made from a thin film in polymer.

The second optical line 18 is an unfolded line.

It is understood by unfolding line that the elements of the second optical line 18 are aligned such as a light beam along the second optical line 18 has a substantially straight path 18A compared to the path of the light beam along the first optical line 16.

In particular, the second optical line 18 is parallel to the gaze direction of the eye 19 of the wearer. For example, the second optical line is parallel to the second direction Y.

The second optical line 18 comprises an optical system 44 adapted to project/transmit a second light signal of the environment on a second area 46 of the retina 19A of the eye of the wearer.

According to special embodiment, the optical system 44 is part of the waveguide 24, named 25. It can further be independent from said waveguide 24. Alternatively, the second optical line 18 arrives directly from the environment to the eye of the wearer.

The limits of this part 25 of the waveguide 24 are defined by the optical field of view angle of the wearer 12.

More precisely, the part 25 is the intersection of the waveguide with the field of view angle of the wearer 12.

The part 25 comprises the output coupler 24C.

The second optical line 18 and the waveguide 24 are arranged so that the light in the second optical line 18 propagates along a general direction which is perpendicular to the main direction of the waveguide 24. For example, the general direction is along the second direction Y.

The two optical lines 16, 18 are arranged so that the intersection between the first area 23 and the second area 46 of the retina 19A is void. The space between the first and second areas 23, 46 is called "void area 48".

Alternatively or in combination with the previous arrangements, the two optical lines 16, 18 are arranged so that the second area 46 surrounds the first area 23.

According to special embodiment, the viewing apparatus 10 comprises at least one lens to correct vision defects, such as for example eye glass lens. Such lens to correct vision defects are preferably located on optical line 16 between output coupler 24C and the eye of the wearer and/or optical line 18 before eye of the wearer.

According to special embodiment, the viewing apparatus 10 comprises at least one optical filter, for example colored optical filter. Such a filter can be located along the optical line 16 (for example between the collimating lens 28 and the total internal reflection prism 30, and/or between the total internal reflection prism 30 and the digital micromirror device 32, and/or between the DMD and the projecting lens 42, and/or between the projecting lens and the waveguide 24) and/or along the optical line 18.

The operating of the viewing apparatus 10 is now described in reference to a method for projecting light signals on an eye of the wearer.

According to special embodiment, the viewing apparatus 10 is in the form of a pair of spectacles.

The method comprises a step of providing, a step of positioning and two steps of projecting.

During the step of providing, the viewing apparatus 10 is provided to the wearer 12.

As a specific example, an eye professional gives the viewing apparatus 10 to the wearer 12.

At the step of positioning, the wearer takes the viewing apparatus and positions it on his head in front of his eyes.

For instance, when the viewing apparatus 10 comprises a fixing band, the wearer 12 uses the fixing band to have the viewing apparatus 10 fixed on his head.

The two steps of projecting are achieved simultaneously.

According to the first step of projecting, a first light signal is projected with the first optical line 16 on the first area 23 of the retina 19A.

The first light signal to be projected is generated by the light signal generator 20.

More precisely, incident light beams 31 generated from the fibered LED 26 are transmitted to the TIR prism 30.

Light beams 31 are reflected by the reflection face 30C of the input prism 30 toward the micromirror device 32.

In function of the position of the micromirrors of the micromirror device 32, the light beam is split into a selected part, reproducing the light signal to be projected, and a discarded part.

The selected part is projected through the output prism $30_2$.

The light beam emerging from the output face 30B is transmitted to the projecting lens 42.

The light beam exiting the projected lens 42 is transmitted to the waveguide 24 through the input coupler 24B.

The body 24A of the waveguide 24 conveys the light beam to the output coupler 24C whereby the light beam is exiting the waveguide 24.

The light beam exiting the output coupler is projected in the first area 23 of the retina of the wearer 12.

Simultaneously, the method comprises the second step of projecting.

According to the second step of projecting, an environment light signal (i.e. second light signal) is projected with the second optical line 18.

Light beams from the environment passes through the body 24A of the waveguide 24 and reach the second area 46 of the retina 19A.

The light beams from the environment are transmitted into the body 24A by the exterior face 24E, cross the body 24A and come out the waveguide by the output coupler 24C and are projected onto the second area 46 of the retina 19A.

The waveguide 24 will keep the peripheral vision of the patient intact while enabling the light signal generator 20 to be placed away from the wearer's visual field.

Using a fibered LED 26 together with a reflection prism 30 also makes it possible to have the LED away from the projecting system thus reducing heating problems for the wearer 12.

Moreover the second light signal projected with the second optical line 18 completes light signal projected with the first optical line for rebuilding a part of the environment.

Moreover, thanks to the second optical line 18, it is ensured that the second light signal is projected on a second area 46 of the retina 19A which does not have any overlap area with the first area 23 of the retina 19A.

Moreover, the viewing apparatus 10 of the invention enables to obtain a device independent of pupil size especially if pupil size is above 3 millimeters (mm) in diameter.

The viewing apparatus 10 also allows delivering the necessary irradiance to the retina 19A of the wearer 12.

The viewing apparatus 10 is also compact. In particular, as the first optical line 16 is a folded line, it is possible to bring the elements of the first optical line 16 closer to the waveguide 24.

Thus the dimension of the viewing apparatus along the second direction is reduced compared to known viewing apparatus.

Such viewing apparatus also provides the wearer with a field of view of 20°×30° thanks to the use of the whole apparatus 10 and notably the TIR prism 30 with the digital micromirror device 32

The viewing apparatus 10 does not obscure the patient's visual field.

According to a specific embodiment, the projecting system (22) and/or the light signal generator (20) are mounted on the frame of a pair of spectacles.

The viewing apparatus 10 may be used in the field of vision restoration using vision prostheses such as retinal implants.

According to a specific embodiment, the viewing apparatus 10 is an apparatus adapted for optogenetics.

The apparatus 10 defined above may be used for the subjects (i.e. wearer) suffering of photoreceptor loss or degeneration, such as in case of retinitis pigmentosa (RP) or macular degeneration (MD). As mentioned above, these affections diminish visual acuity, diminishes light sensitivity, or result in blindness of a part of the field of view of the subject.

As explained above, some therapies consist in stimulating transfected cells of the retina and/or retinal implants with a light beam.

The first area 23 of the retina on which the light signal with the first optical line 16 is intended to be projected comprise cells, more specifically retinal cells, that have been genetically modified for expressing light-gated ion channel protein for optogenetic therapy.

According to special embodiment, said light-gated ion channel protein is chosen in the group consisting of Chrimson, ChrimsonR, (WO2013/71231), ChrimsonR-tdT (WO2017/187272), Catch, Channelrhodopsin (US20140121265, U.S. Pat. No. 8,906,360), and melanopsin and derivatives thereof.

The first area 23 of the retina on which the light signal with the first optical line 16 is intended to be projected comprises retinal implant having to be stimulated.

The area of the retina is stimulated by a light beam reproducing light signal, more specifically an image, of the environment.

The projected light signal rebuilds the lost field of view due to the photoreceptor loss or degeneration in function of the gaze direction of the subject.

The light beam obtained with the first optical line and stimulating the parts of the retina is obtained by the method explained above.

In the detailed embodiment, the environment light signal, more specifically the image, projected with the second optical line 18 corresponds to the part of the environment that complete the light signal, more specifically the image, projected with the first line in such a way that the wearer sees a rebuilt light signal, more specifically the image, of the environment.

Moreover, the first area 23 of the retina is stimulated with the required light characteristics independent of the pupil size.

In such case, it is to be noted that thresholds of light intensity (maximum and minimum) are given by phototoxicity standards and are further analyzed in literature relevant to ophthalmology or to the application of light stimulation for an optogenetic therapy (Yan et al. 2016; Delori, Webb, and Sliney 2007; Sliney et al. 2005). For example, for a light with a wavelength of 595 nm, the maximum light intensity at the retina is 7 mW/mm$^2$ (ISO 15004-2 2007; ISO 62471 2006), and At the cornea (anterior segment), the maximum light intensity is 32 mW over any 1 mm diameter disc (ISO 15004-2 2007).

In addition, the retinal radiant exposure limit when taking into account the luminance dose restriction is 6.6 J·cm$^{-2}$ over 48 hours (luminance dose restriction, ANSI Z136.1 2014).

According to another particular example, the viewing apparatus is adapted for a virtual reality apparatus. Head-Mounted displays are used for example used for augmented reality, for virtual reality or for movie display.

In such case, the light signal projected with the second optical line 18 generally has no specific link with the environment.

The viewing apparatus and the method disclosed in relation to the viewing apparatus 10 can be used for virtual reality or optogenetic applications.

The invention claimed is:

1. A viewing apparatus comprising:
    a first optical line comprising:
    a projecting system adapted to project a first light signal on a first area of the retina of an eye of a wearer of the viewing apparatus,
    a light signal generator generating the first light signal to be projected, and
    a waveguide comprising an input coupler and an exit coupler,
        wherein the waveguide comprises a body and is adapted to convey light from the input coupler to the exit coupler;
        wherein the input coupler and the output coupler are arranged on an inside face of the body; and
        wherein the input coupler and the output coupler are made from a thin polymer film having a thickness less than 10 micrometers.

2. The viewing apparatus according to claim 1, wherein the viewing apparatus further comprises a second optical line comprising an optical system adapted to project a light signal of the environment on a second area of the retina of the eye of the wearer.

3. The viewing apparatus according to claim 2, wherein the two optical lines are arranged so that the intersection between the first area and the second area is void.

4. The viewing apparatus according to claim 2, wherein the two optical lines are arranged so that the second area surrounds the first area.

5. The viewing apparatus according to claim 2, wherein a main direction of light conveyance is defined for the waveguide and wherein the second optical line) and the waveguide are arranged so that the light in the second optical line propagates along a general direction which is perpendicular to the main direction of light conveyance of the waveguide.

6. The viewing apparatus according to claim 2, wherein the second optical line is an unfolded line.

7. The viewing apparatus according to claim 6, wherein the light signal generator comprises a light source and the first optical line a collimating lens, the total internal reflection prism, a digital micromirror device and a projecting lens.

8. The viewing apparatus according to claim 2, wherein the second optical line is parallel to the gaze direction of the eye of the wearer.

9. The viewing apparatus according to claim 1, wherein the waveguide is translucent or transparent.

10. The viewing apparatus according to claim 1, wherein the light signal generator comprises a total internal reflection prism adapted to steer an incident light beam with an angle.

11. The viewing apparatus according to claim 10, wherein the angle is comprised between 20° and 40°.

12. The viewing apparatus according to claim 1, wherein the first optical line is a folded line.

13. The viewing apparatus according to claim 1, wherein the light signal generator comprises a light source, the light source being at least one of a fibered source and an electroluminescent diode.

14. The viewing apparatus according to claim 1, wherein the viewing apparatus is an apparatus for optogenetics uses.

15. The viewing apparatus according to claim 1, wherein the viewing apparatus is a virtual reality apparatus.

16. The viewing apparatus according to claim 1, wherein the field of view of the projecting system extends between 15° and 25° along a first direction and between 25° and 35° along a second direction perpendicular to the first direction.

17. A method for projecting a light signal in an eye of the wearer of a viewing apparatus comprising a first optical line comprising:
    a projecting system adapted to project a first light signal on a first area of the retina of an eye of a wearer of the viewing apparatus,
    a light signal generator generating the first light signal to be projected, and
    a waveguide comprising an input coupler and an exit coupler,
        wherein the waveguide comprises a body and is adapted to convey light from the input coupler to the exit coupler; and
        wherein the input coupler and the output coupler are arranged on an inside face of the body; and
        wherein the input coupler and the output coupler are made from a thin polymer film having a thickness less than 10 micrometers.

18. The method according to claim 17, wherein the viewing apparatus further comprises a second optical line comprising an optical system adapted to project a light signal of the environment on a second area of the retina of the eye of the wearer, the method comprising simultaneously a step of projecting a light signal with the first optical line and a step of projecting an environment light signal with the second optical line.

* * * * *